United States Patent
Miller et al.

[11] Patent Number: 5,827,947
[45] Date of Patent: Oct. 27, 1998

[54] PIEZOELECTRIC SENSOR FOR HYDRIDE GASES, AND FLUID MONITORING APPARATUS COMPRISING SAME

[75] Inventors: Cynthia A. Miller, Brookfield; Glenn M. Tom, New Milford, both of Conn.

[73] Assignee: Advanced Technology Materials, Inc., Danbury, Conn.

[21] Appl. No.: 785,342

[22] Filed: Jan. 17, 1997

[51] Int. Cl.$^6$ .......................... G01N 31/02; G01N 31/22; G01N 30/00

[52] U.S. Cl. ..................... 73/24.06; 73/31.06; 423/210; 502/402

[58] Field of Search .......................... 73/24.01, 24.03, 73/24.04, 31.05, 31.06, 24.06, 23.21, 61.79, 64.53; 423/210, 219; 502/400, 401, 402; 210/500.25

[56] References Cited

U.S. PATENT DOCUMENTS

| | | | |
|---|---|---|---|
| 4,446,720 | 5/1984 | Sinclair | 73/23 |
| 5,037,624 | 8/1991 | Tom et al. | 423/210 |
| 5,065,140 | 11/1991 | Neuburger | 73/23.31 |
| 5,138,869 | 8/1992 | Tom | 73/31.03 |
| 5,151,110 | 9/1992 | Bein et al. | 55/75 |
| 5,151,395 | 9/1992 | Tom | 502/67 |
| 5,320,817 | 6/1994 | Hardwick et al. | 423/237 |
| 5,339,675 | 8/1994 | DiLeo et al. | 73/24.04 |
| 5,385,689 | 1/1995 | Tom et al. | 252/194 |
| 5,445,008 | 8/1995 | Wachter et al. | 73/24.06 |
| 5,573,728 | 11/1996 | Loesch et al. | 422/90 |

OTHER PUBLICATIONS

Neuburger, Glen G., "Detection of Ambient Hydrogen Chloride with a Zinc–Coated Piezoelectric Crystal Resonator Operating in a Frequency–Time Different Mode," Anal. Chem. 1989, 61, 1559–1563.

Levenson, Leonard L., "II. Chemisorption on Single Element Thin Films," in *Applications of Piezoelectric Quartz Crystal Microbalances*, C. Lu, editor, vol. 7, Elsevier, Amsterdam, 1984, pp. 198–203.

*Primary Examiner*—Christine K. Oda
*Assistant Examiner*—Rose M. Miller
*Attorney, Agent, or Firm*—Steven J. Hultquist; Oliver A. M. Zitzmann

[57] ABSTRACT

A sensor element for detection of a trace fluid component in a fluid stream or other fluid environment, comprising a piezoelectric crystal having a fundamental resonant frequency in response to an applied oscillating electric field, and an inert porous material coating on the piezoelectric crystal containing a metal species which is reactive with the trace fluid component to yield a solid interaction product of changed mass in relation to initial mass of the metal species interacting with the trace fluid component to yield the solid interaction product. Such sensor element may be employed in a sensor apparatus for applying an oscillating electric field to the piezoelectric crystal which generates an output resonant frequency therefrom, together with (i) sampling the output resonant frequency of the piezoelectric crystal, (ii) determining the change in resonant frequency occurring on formation of the solid interaction product, and (iii) generating an output indicative of the presence of the trace fluid component in the fluid environment. The sensor may be utilized for detection of hydride gases in environmental gas monitoring applications, as well as in end point detectors in scrubbing and other gas processing operations.

28 Claims, 11 Drawing Sheets

PIEZOELECTRIC SENSOR FOR HYDRIDE GASES, AND FLUID MONITORING APPARATUS COMPRISING SAME

BACKGROUND OF THE INVENTION

1. Field of the Invention

The present invention relates to a sensor for detection and monitoring of low/trace concentrations of gas components such as hydrides in fluids potentially containing such components, and to a fluid processing apparatus and method utilizing same. The sensor apparatus and method of the invention have utility, inter alia, as either a single or multicomponent environmental monitor, or as an end point sensor, e.g., for the semiconductor manufacturing industry.

2. Description of the Related Art

In the semiconductor manufacturing industry and in other industrial process and manufacturing fields, a number of systems and techniques have been developed for monitoring a fluid, e.g., a process stream or an ambient environment in a plant facility, for the presence of a hazardous or otherwise deleterious gas components. Applications in which such fluid monitoring is carried out include monitoring of ion implant cabinets for hydride and acid gases, monitoring of process streams to determine the end point utility of a scrubber medium employed for treatment of such streams to remove hazardous gas components therefrom, and monitoring of room air for toxic gas components.

In the conventional use of dry scrubbers, i.e., sorbent beds that reactively remove undesired components of gas streams flowed therethrough, it is critically important that the approach of the bed to exhaustion of its removal capacity be accurately determinable. If the exhaustion of the removal capability of the bed is not detected by operating personnel, then gas requiring treatment will pass untreated through the bed and be passed to discharge, disposal or other process steps, still containing the components desired to be removed from such treatment effluent.

Such non-treatment, or inadequate treatment as the point of exhaustion is approached, may entail severe consequences. By way of example, dry scrubbers are used extensively in the semiconductor manufacturing industry, where the scrubber is employed to abate hazardous gases from the effluent from the processing plant, or its subunits. The failure to detect exhaustion of the scrubber bed thus may result in deleterious exposure of plant personnel to hazardous gases, as well as environmental contamination in the ambient surroundings of the semiconductor process facility. Additionally, incidents have been reported in which eductor devices downstream of scrubbers have experienced plugging when impurities have broken through the scrubbers without being detected.

Accordingly, it has been common practice either to require change-out of the scrubber bed, viz., replacement of the scrubber material in the bed with fresh scrubber medium, well prior to the actual exhaustion of the scrubber bed, i.e., with a substantial safety margin in respect of the operating life of the scrubber bed, or else to deploy monitors that detect actual or incipient breakthrough of the scrubbable components in the gas stream discharged from the scrubber bed.

The first alternative, of change-out of the scrubber material well in advance of the exhaustion of the capacity of the scrubber bed, although effective in terms of preventing discharge of scrubbable components in the effluent gas, is inefficient in respect of the wastage of scrubber medium which could otherwise be employed to remove the scrubbable component, i.e., effective capacity of the scrubber bed is not utilized. As a result, the scrubber bed must be oversized to accommodate the unused scrubber material.

The second alternative, of using monitors that detect actual or threshold breakthrough of the scrubbable components in the scrubber beds, is expensive, involving the use of costly devices which additionally require significant maintenance (with replacement of consumable elements, e.g., the frequent change of color tapes in so-called MDA monitors, or frequent change of cells in monitors such as those commercially available under the trademark Enmet—MDAs require biweekly paper tape changes and Enmets require monthly cell changes and in-line calibration with live gases), requires in-line recalibration not infrequently, and in some instances does not measure the impurity species properly since the MDAs and Enmets were not developed for this purpose. In general, problems of cost, accuracy and reliability plague the existing commercially available monitors in application to scrubbing systems. The development of an inexpensive and reliable end point sensor for hydride gases would therefore be a major advantage for such dry scrubbing systems.

Another application in which the detection of low or trace concentrations of impurities is carried out is the monitoring of air or other ambient gases for the presence of trace hazardous gases. The systems currently commercially available such as the aforementioned MDA monitors, or Kitagawa tubes, are either costly or else do not provide useful readouts.

More specifically, users of such devices have found that the current monitors either falsely alarm or do not alarm at all, especially if this routine recalibration is not completed. The results in clogging of the lines and process equipment such as eductors, which leads to expensive shutdown periods for cleaning the process facility lines.

In addition, in such ambient gas monitoring operations, a conventional MDA will require paper tape changes every couple of weeks, and thus entails a relatively short operating life and significant ongoing maintenance. It would therefore be an improvement in the art of environmental gas monitoring to provide a monitoring apparatus which requires little routine maintenance (e.g., once every 6 months vs. once every 2 weeks for a typical MDA monitor), has a cost which is significantly less than the cost of an MDA, and possesses a sensitivity and accuracy which is at least as good as the sensitivity and accuracy of an MDA, as well as possessing the capability to provide extended time-weighted average data for leakage rates for purposes of regulatory compliance.

In sum, it would be a significant advance in the art, and is therefore an object of the present invention to provide a low cost, accurate, reliable, and easily fabricated and operated sensor device for monitoring of impurity species such as hydride gases in fluid environments, such as gas streams discharged from a scrubber bed, or ambient gas environments which are monitored for the presence of contaminants.

It is another object of the present invention to provide a solid state gas detection apparatus and method based on chemisorption, utilizing quartz piezoelectric devices with specialty coatings designed to possess high sensitivity and selectivity for hydride gases such as arsine, phosphine, silane and diborane.

It is another object of the invention to provide a highly sensitive and selective detection system for determining the presence of impurity species in fluid environments.

It is a further object of the invention to provide an end point detector for sensing the breakthrough of impurity species in such operations as dry scrubbing of process gases.

Other objects and advantages of the invention will be more fully apparent from the ensuing disclosure and appended claims.

SUMMARY OF THE INVENTION

The present invention relates to a piezoelectric sensor, and to a gas monitoring apparatus and method utilizing same.

In one aspect, the present invention relates to a sensor element for detection of a trace fluid component in a fluid environment, comprising:

a piezoelectric crystal having a fundamental resonant frequency in response to an applied oscillating electric field;

an inert porous material coating on the piezoelectric crystal containing a metal species which is reactive with the trace fluid component to yield a solid interaction product of changed mass, in relation to initial mass of the metal species interacting with the trace fluid component to yield the solid interaction product.

Another aspect of the invention relates to a sensor apparatus including such sensor element and further comprising:

means for applying an oscillating electric field to the piezoelectric crystal which generates an output resonant frequency therefrom; and means for (i) sampling the output resonant frequency of the piezoelectric crystal while the oscillating electric field is applied thereto, (ii) determining the change in resonant frequency from the fundamental resonant frequency that occurs on formation of the solid interaction product when the metal species interacts with the trace fluid component in the fluid environment, and (iii) generating an output indicative of the presence of the trace fluid component in the environment.

Such apparatus may further comprise means for flowing fluid from the fluid environment to the coating on the piezoelectric crystal so that the trace fluid component when present reacts with the metal species to form the solid interaction product.

The fluid environment to which the sensor element, apparatus and process of the invention are applicable includes ambient fluids as well as fluids generally, in static or motive volumes, and process streams, and encompass vapors as well as gases. The trace fluid component may be constituted by any suitable gas species which is reactive with the metal species in the inert porous material coating on the piezoelectric material, to produce a solid reaction product of changed mass, in relation to initial mass of the metal species interacting with the trace fluid component to yield the solid interaction product. Such trace fluid component may for example comprise a vapor or gas containing Group III–VII element(s) of the Periodic Table, such as are widely encountered in the manufacture of semiconducting materials and semiconductor devices.

The coated piezoelectric crystal may for example exhibit a frequency response rate to the trace fluid component in the range of from about 0.001 to about 100,000 milliHertz/min/(part-per-million of the fluid component). Preferably the coated piezoelectric crystal exhibits a frequency response rate to the trace fluid component in the range of from about 0.01 to about 10,000 milliHertz/min/(part-per-million of the fluid component); more preferably, such range is from about 0.1 to about 5000 milliHertz/min/(part-per-million of the fluid component); and most preferably such range is from about 1 to about 1000 milliHertz/min/(part-per-million of the fluid component).

The means for flowing fluid from the fluid environment to the coating on the piezoelectric crystal may for example comprise a passage having appropriate geometry, e.g., length to diameter characteristics, and/or containing a flow limiting structure such as a frit or flow-restricting orifice, so that the flow of fluid to the coating is maintained at a level which is consistent with good sensitivity and useful sensor life. Alternatively, in the case of environmental monitoring applications, the apparatus may be constructed and arranged to selectively expose the reactive coated piezoelectric crystal to the ambient environment, e.g., by a manually openable valve or sampling port, for periodic gas sampling. As a still further alternative, the sensor may be open to the ambient environment for contact with the environmental gases, without any such flow restriction and/or exposure/closure structure.

In the sensor element of the invention, the metal species may include a metal or a metal compound which is reactive with the fluid component of interest, producing a reaction product whose mass relative to the initial metal species is changed to effect a dynamic frequency response variation in the piezoelectric crystal. Such frequency response variation is quantitatively correlatable to indicate the presence and concentration of the fluid component of interest in the sensed or monitored gas environment.

The metal moiety of the metal compound used as the reactive species in the sensor of the invention may for example be silver, copper, calcium, chromium, manganese, sodium, iron, etc. The metal compound may be a salt (e.g., a halide salt, a nitrate, etc.), an oxide, or other compound or elemental metal per se, which is reactive with the fluid component to be monitored or sensed, to produce the requisite frequency response change in the piezoelectric crystal on which the inert porous material coating containing the metal species is disposed, when the sensor element is contacted with the fluid component of interest.

The inert porous material coating may be formed of any suitable inert material such as for example activated or unactivated carbon, silica, silicon, alumina, crystalline aluminosilicates, kieselguhr, and inert macroreticulate polymers such as the styrene-divinylbenzene polymer matrix commercially available under the trademark "Amberlite" from Rohm & Haas, Inc. (Philadelphia, Pa.). The metal species which is reactive with the fluid component of interest is incorporated (e.g., dispersed) in the inert porous material coating in any suitable manner, e.g., by loading of the metal species in the pores and on the surfaces of the porous material coating from a fluid (vapor or liquid) source of the metal species, by coprecipitation of the inert porous material and the metal species on the piezoelectric crystal substrate surfaces, by ion implantation of the metal ions of the metal species of interest and subsequent reaction of the metal ions with a coreactant producing a metal compound having the desired reactivity with the fluid component of interest, by sol gel formation of the inert porous material coating with the sol gel containing the metal compound or a precursor thereof, or by independent fabrication of the inert porous material layer containing the metal species, e.g., etching of a continuous film of the inert material to render same porous and impregnating the film with the metal species, following the fabrication of which the impregnating coating film is transferred to and bonded with the surface of the piezoelectric crystal.

The porosity and pore size characteristics of the inert porous material may be widely varied in the broad practice of the invention, to achieve the desired degree of sensitivity/ reactivity of the metal species which is loaded on the inert porous material. Generally, the inert porous material may have a void fraction of from about 0.05 to about 0.95, based on the total volume of such material, with pores generally being in the range of from about 2 Angstroms to about 200 Angstroms or more, and with such material having a surface area, as measured by BET nitrogen isotherm, on the order of from about 10 square meters/gram of material to about 1500 square meters/gram of material.

The specific porosity characteristics, void fraction, and type of porous material and reactive metal species for a given application of the piezoelectric sensor of the present invention may be readily determined without undue experimentation by the empirical generation of response curves for the specific materials, conditions and characteristics involved, as hereinafter described in greater detail in respect of illustrative embodiments of the invention.

By way of specific illustrative example, the piezoelectric crystal in the sensor element of the invention may for example comprise a piezoelectric silica (quartz) crystal. Useful piezoelectric crystals include those having a fundamental resonant frequency in the range of from about 1 Megahertz to about 20 Megahertz.

In a preferred aspect, the piezoelectric sensor of the present invention comprises a piezoelectric crystal on which the inert porous material coating containing the reactive metal species is formed by sol gel processing, wherein the sol contains the metal species or a precursor thereof. The metal species-containing sol gel dispersion is applied to the surface of the piezoelectric crystal and allowed to dry to a thin film of the desired sensing matrix material or a precursor thereof.

In the sensor apparatus of the invention, comprising a sensor element as hereinabove described, the means for (i) sampling the output resonant frequency of the piezoelectric crystal while the oscillating electric field is applied thereto, (ii) determining the change in resonant frequency from the fundamental resonant frequency that occurs on formation of the solid interaction product when the sensor material interacts with the trace fluid component in the fluid environment, and (iii) generating an output indicative of the presence of the trace fluid component in the environment, may for example comprise means such as a circuit including therein a cascaded array of frequency counters, or other electronics suitable for such purpose.

The sensor apparatus may be constructed and arranged so that the output indicative of the presence of the fluid component of interest in the fluid stream or the fluid environment, comprises a calculated concentration of such fluid component therein.

In one embodiment of the invention, the sensor further comprises a flow control means for controllably flowing a selected flow rate of fluid from the fluid environment into contact with the reactive species material on the piezoelectric crystal, and the aforementioned means for performing functions (i), (ii) and (iii), comprise computational means for determining the calculated concentration of the specific fluid component in the fluid medium being sensed or monitored, in accordance with a suitable algorithm.

The sensor apparatus of the invention in another embodiment further comprises a flow passage accommodating flow therethrough of fluid of the fluid environment, and having a diffusional flow restrictor in the passage, arranged in relation to the sensor material to permit substantially only diffusional flow from the flow passage through the diffusional flow restrictor to the reactive metal species. Such diffusional flow restrictor desirably is constructed and arranged to prevent particulate solids in the fluid environment from contacting the metal species of the sensor element.

The sensor apparatus may further comprise means for removing substantially all metal species-interactive components other than the selected fluid component from the fluid, before the fluid contacts the reactive metal species constituting the sensor material. Such removing means may advantageously comprise a chemisorbent medium having sorptive affinity for metal species-interactive components other than the selected fluid component. As used herein, the term "metal species-interactive" refers to gaseous or fluid components in the sensed or monitored medium which are reactive with the metal species contained in the inert porous material on the piezoelectric crystal of the sensor element.

In another aspect, the invention relates to a fluid scrubbing assembly for processing of impurity-containing fluid, comprising:

a scrubber vessel containing a dry scrubber composition having sorptive affinity for impurity in the impurity-containing fluid;

means for introducing impurity-containing fluid to the scrubber vessel for contacting with the dry scrubber composition therein to remove impurity from the impurity-containing fluid, and yield treated fluid;

means for discharging treated fluid from the scrubber vessel;

a sensor for detection of impurity in the treated fluid, such sensor comprising:

(I) a piezoelectric crystal having a fundamental resonant frequency in response to an applied oscillating electric field;

(II) an inert porous material coating on the piezoelectric crystal containing a metal species sensor material which is reactive with the impurity to yield a solid interaction product of changed mass in relation to mass of the sensor material interacting with the impurity to yield the solid interaction product;

(III) means for applying an oscillating electric field to the piezoelectric crystal which generates an output resonant frequency therefrom;

(IV) means for (i) sampling the output resonant frequency of the piezoelectric crystal while the oscillating electric field is applied thereto, (ii) determining the change in resonant frequency from the fundamental resonant frequency upon formation of the solid interaction product when the metal species sensor material interacts with impurity in the treated fluid, and (iii) generating an output indicative of the presence of the impurity in the treated fluid; and means for flowing at least a portion of the treated fluid to the sensor for determining, by the output indicative of the presence of impurity, when breakthrough of impurity has occurred in the dry scrubber composition in said vessel.

A further aspect of the invention relates to a process for monitoring a fluid stream for determining presence of a selected component therein, such process comprising:

providing a sensor for detection of the selected component in the fluid stream, such sensor comprising:

(A) a piezoelectric crystal having a fundamental resonant frequency in response to an applied oscillating electric field;

(B) an inert porous material coating on the piezoelectric crystal containing a metal species sensor material which is reactive with the selected component to yield a solid interaction product of changed mass in relation to initial mass of the sensor material interacting with the selected component to yield the solid interaction product;

applying an oscillating electric field to the piezoelectric crystal which generates an output resonant frequency therefrom;

sampling the output resonant frequency of the piezoelectric crystal while the oscillating electric field is applied thereto;

determining the change in resonant frequency from the fundamental resonant frequency upon formation of the solid interaction product when the metal species sensor material interacts with the selected component in the fluid stream; and generating an output indicative of the presence of the selected component in the fluid stream.

In such process, the step of generating the output indicative of the presence of the selected component in the fluid stream may for example, comprise determining via a programmed computer a calculated concentration of the selected component in the fluid stream.

The process may further comprise controllably flowing at least a portion of the fluid stream at a selected flow rate in contact with the sensor material on the piezoelectric crystal, and determining the calculated concentration of the selected component in the fluid stream, in accordance with a suitable algorithm.

In the process of the invention, the selected component, of the fluid which is detected or monitored may for example comprise a hydride gas such as diborane, arsine, phosphine, silane, germane, etc.

The process of the invention may be carried out with the sensor being constructed and arranged to be contacted by only a restricted part or portion of a main gas flow stream in a process system, so that the cumulative concentration of the impurity species reactive with the metal species in the coating of inert porous material on the piezoelectric crystal does not rapidly consume the coating and deplete the capacity of the sensor to detect the impurity species over a useful lifetime of operation.

In another aspect, the coated crystal is arranged in the sensor apparatus in relation to the fluid flow stream so that the coated piezoelectric crystal exhibits a frequency response rate to the trace fluid component in the range of from about 0.001 to about 100,000 milliHertz/min/(part-per-million of the fluid component), preferably in the range of from about 0.01 to about 10,000 milliHertz/min/(part-per-million of the fluid component), more preferably in the range of from about 0.1 to about 5,000 milliHertz/min/(part-per-million of the fluid component), and most preferably in the range of from about 1.0 to about 1000 milliHertz/min/(part-per-million of the fluid component). Such arrangement may for example entail the sampling by the coated piezoelectric crystal of a slip-stream or side-stream of a main flow of process fluid, or the restricted access of the main flow of fluid to the coated piezoelectric crystal.

In another aspect, the invention relates to a fluid scrubbing process for treating impurity-containing fluid, comprising:

contacting impurity-containing fluid with a dry scrubber composition to remove impurity from the impurity-containing fluid, and yield treated fluid;

detecting impurity in the treated fluid, by the steps comprising:

providing:

(I) a piezoelectric crystal having a fundamental resonant frequency in response to an applied oscillating electric field; and (II) an inert porous material coating on the piezoelectric crystal of a metal species which is reactive with the impurity to yield a solid interaction product of changed, e.g., increased or decreased, mass in relation to initial mass of the metal species interacting with the impurity to yield the solid interaction product;

applying an oscillating electric field to the piezoelectric crystal which generates an output resonant frequency therefrom;

sampling the output resonant frequency of the piezoelectric crystal while the oscillating electric field is applied thereto;

determining the change in resonant frequency from the fundamental resonant frequency incident to the formation of the solid interaction product when the metal species interacts with impurity in the treated fluid;

generating an output indicative of the presence of the impurity in the treated fluid; and flowing at least a portion of the treated fluid to the sensor for determining, by the output indicative of the presence of impurity, when breakthrough of impurity has occurred in the dry scrubber composition.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
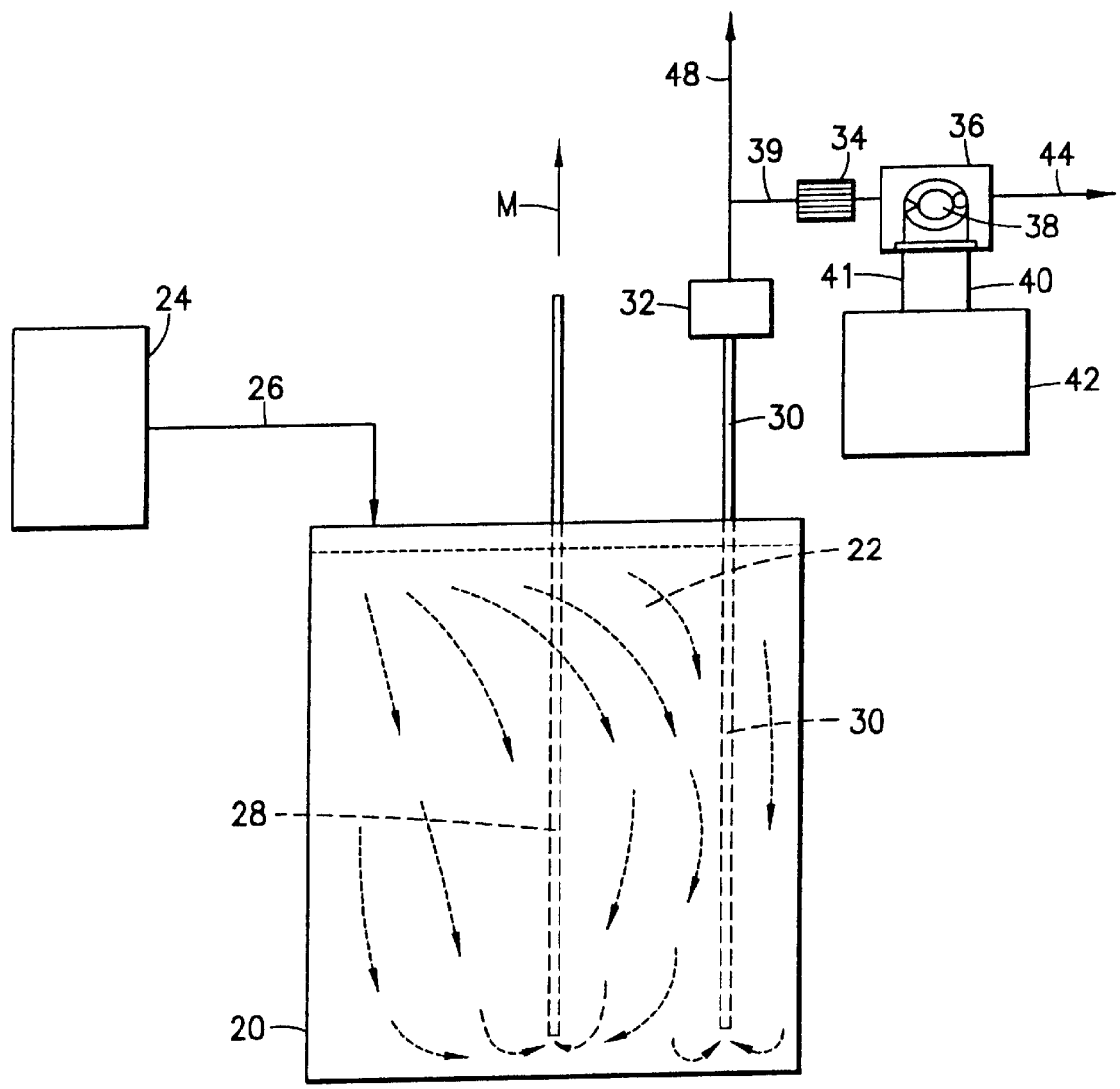
FIG. 1 is a schematic view of a process system featuring a piezoelectric crystal sensor assembly according to one embodiment of the invention.

The disclosures of U.S. patent application Ser. Nos. 08/678,572 filed Jul. 12, 1996 and 08/679,258 filed Jul. 12, 1996 are hereby incorporated herein by reference in their entirety.

The present invention utilizes piezoelectric crystals coated with an inert porous material coating containing a metal species which is reactive with the fluid impurity of interest, reacting to form a reaction product whose solid product(s) on the piezoelectric crystal substrate have a different cumulative mass than the starting metal species, so that the frequency response characteristics of the piezoelectric crystal is altered in a manner which can be sensed, and preferably quantitated, to determine the presence and the concentration of the fluid impurity.

The sensor element of the invention comprises a metal species such as compounds of silver, chromium, copper, calcium, manganese, sodium, iron, etc., contained in the pores and on the surfaces of the inert porous material, to provide highly sensitive detectors for gaseous hydrides, halides and other gases, when the fluid being sensed or monitored is contacted and reacted with the reactive metal species sensor material under operating conditions.

In the sensor of the invention, the piezoelectric crystal coated with the inert porous material coating containing the metal species sensor material is subjected to an input frequency, such as by an appropriately constructed and arranged oscillator circuit coupled in operative relationship to the piezoelectric crystal. The output frequency of the piezoelectric crystal coated with the metal species sensor material then is monitored and the change of the frequency in relation to the natural harmonic frequency of the coated crystal is determined, e.g., by a cascaded counter assembly.

By this arrangement, the contacting of a fluid component of interest with the metal species in the inert porous coating material on the crystal will cause reaction to yield a reaction product of different mass than the initial mass of the metal component on the crystal. As a result of such mass change, the frequency response characteristics of the coated crystal will change, and this frequency change thus will reflect the presence of the hydride, or other desired component, in the gas contacted with the coating film on the piezoelectric crystal.

The fluid component of interest which is monitored or detected by the sensor of the invention may be any suitable vapor or gas component(s) such as gases containing Group III–VII elements of the Periodic Table. An illustrative listing of gas compounds containing Group III–VII constituent elements, include, but are not limited to, gas compounds set out below.

Group III:
Organic compounds of aluminum, gallium, and indium; hydrides of boron; gallanes, alanes, indanes and their Lewis Base complexes, e.g. trimethylamine-gallane, trimethylamine-alane.

Group IV:
Silane, and chlorosilanes ($SiH_{4-x}Cl_x$, wherein x is an integer whose value is 1 to 4 inclusive); germane; and certain fluorinated etching agents and products; akylsilanes and alkylgermanes.

Group V:
Hydrides of nitrogen, phosphorus, and arsenic; alkyl arsine and alkyl phosphine compounds.

Group VI:
Hydrides of sulfur, selenium, and tellurium; alkyl selenium and alkyl tellurium compounds.

Group VII:
Hydrogen halides (fluoride, chloride, bromide, and iodide), boron halides ($BCl_3$, $BF_3$), and chlorine ($Cl_2$).

In respect of the Group III–VII gaseous compounds, illustrative metals of the metal species potentially useful in the sensor of the invention are set out by way of example in the table below:

| Gas Compounds Containing Elements of: | Illustrative Metals of the Reactive Metal Species: |
|---|---|
| Group III | Ag, Cu, Cr, Mn, Fe |
| Group IV | Ag, Cu, Cr, Mn, Fe |
| Group V | Ag, Cu, Cr, Mn, Fe |
| Group VI | Ag, Cu, Cr, Mn, Fe |
| Group VII (HX) | MX' or MX"$_2$, ZnO |

In the case of Group VII element-containing gases, the corresponding metal halide compounds of the table are compounds which are suitably dispersible into the inert porous matrix material and react with the Group VII compound to produce an irreversible mass change. M is a metal selected from Groups IA, IB, IIA and IIB of the Periodic Table. An example of such reaction is the metathesis reaction MX'+HX→MX+HX', wherein M=Ca, X'=I and X=Cl or F. Another example is M=Na, X'=tosylate, bicarbonate, oxide or carbonate, and X=Cl or F.

Preferably, when the fluid component of interest in a hydride, the metal species comprises a metal oxide or a metal nitrate which is reactive with the hydride gas, e.g., arsine, phosphine, silane, germane, diborane, etc., in a redox reaction to reduce the metal compound to yield an elemental metal product, and either nitric acid or water, depending on whether the metal species is a nitrate or an oxide of the metal.

In the sensor element of the invention, the inert porous material coating must adhere to the surface of the piezoelectric crystal in a uniform manner and should not exceed the mass loading limit of a crystal as that would dampen the oscillator. In order for sensors of the invention to have long lifetimes the active metal species is contained in a high surface area layer of an inert porous material. The response curve of the sensor element must be immediate, reproducible and linear.

Thus, in relation to the piezoelectric sensors and quartz microbalance monitors of the prior art, the present invention achieves a significant advance in the art, by dispersing an active reactant (metal) species in a high surface area inert porous material matrix, so that the active reactant is more slowly consumed in reaction than would be the case if the reactive metal species were to be provided in a thin metal compound film directly on the piezoelectric crystal's surface. The porosity of the inert material permits the active metal species to be readily deposited in a reactive form on the surfaces and in the pores of the porous material, by solution deposition, chemical vapor deposition, precipitation, or other suitable method of formation of the porous material matrix containing the reactive metal species.

The invention thus contemplates binding a reactive component to the crystal surface in a porous matrix to detect hydride or other impurity gases reactive with the metal species in the porous material coating.

As an example of the present invention, a silver salt may be suspended in a sol gel matrix and employed to form an inert porous material coating on a surface of a piezoelectric crystal, thereby providing a support matrix which binds the silver salt in a manner allowing gas molecules to diffuse into the surface and react with the silver. The sol gel formulation may be carried out in a suitable manner, including mixing of silicate material such as tetraethylorthosilicate (TEOS), water, solvent, acid, and the metal salt, followed by hydrolyzing the mixture for sufficient time and temperature to permit the deposition of a suitable silica coating containing a metal salt of the desired activity.

The coating of the inert porous material containing the metal salt on the substrate may be carried out by spin coating the sol gel metal salt solution onto the piezoelectric crystal surface. Once both sides of the crystal have been coated, the crystal must be properly stored in order to preserve the sensitivity of the sensor element (e.g., in the case of a silver nitrate-based sensor of the invention, such sensitivity preservation may involve storage of the sensor element in a dessicator in the dark, so that the silver nitrate compound in the inert porous material is protected from light and moisture). The coating technique may be varied to achieve the desired sensor response, by selection and use of the amounts and proportions of TEOS, metal salt, water, solvent and acid added, the hydrolysis time and temperature, the coating technique, the gelation time, the drying time and the type of metal salt employed. Thus, the coating formulation may be widely varied to obtain the desired quality and character of the inert porous material coating containing the reactive metal species.

The sol gel formulation utilized to form the metal species-containing inert porous material coating on the piezoelectric crystal may be made using general sol gel techniques well known and established in the art, e.g., the sol gel techniques disclosed in Bright, F. V., Dunbar, R. A. and Jordan, J. D. Anal Chem. *1996, 68, 604*, "Development of Chemical Sensing Platforms Based on Sol-Gel-Derived Thin Films: Origin of Film Age vs Performance Trade-Offs."

A particularly preferred reactive metal species in the inert porous coating, which is responsive to the presence of arsine, phosphine and silane, as well as diborane, is silver nitrate. All four of arsine, phosphine, silane and diborane are effective reducing agents and will cause a decrease in the mass loading on the piezoelectric crystal when they react with silver nitrate. Table One shows the oxidation reduction reactions of arsine, phosphine, silane and diborane with silver nitrate, and the net change in molecular weight and the standard electrode potentials. A positive $e°$ is indicative of a favorable reaction. The mass change of the reactive species during reaction on the piezoelectric crystal can be negative or positive, in the broad practice of the invention. The sign of the mass change will determine if the frequency increases or decreases upon exposure to the toxic gas component, or other gas impurity or trace component of interest.

TABLE 1

Reduction Oxidation Reactions of Hydride Gases with Silver Nitrate.

| Redox Reactions | $\Delta$g/mol | $e°(V)$ |
|---|---|---|
| $3AgNO_3 + AsH_3(g) \rightarrow 3 Ag + As + 3HNO_3\uparrow$ | −111.5 | 1.41 |
| $3AgNO_3 + PH_3(g) \rightarrow Ag + 3P + 3HNO_3\uparrow$ | −155.4 | 0.91 |
| $4AgNO_3 + SiH_4(g) \rightarrow Ag + 4Si + 4HNO_3\uparrow$ | −219.9 | favorable |
| $6AgNO_3 + B_2H_6(g) \rightarrow 2 Ag + 6B + 6HNO_3\uparrow$ | −350 | favorable |

Other metals which are reduced by arsine, silane, phosphine and diborane would also be suitable for sensing of the presence of hydride gases, as for example high valent metals such as copper, manganese, chromium, iron, etc. When sol gel techniques are used to form the inert porous material coating for a metal salt, the key parameter necessary to incorporate metal salts into the sol gel coating matrix is the solubility of the metal salt.

Cu(II) is also a viable metal species for a hydride sensor. Set out in Table Two below is the oxidation potential for reduction of CuO with arsine and phosphine, as well as the weight changes and reactions with arsine, phosphine, silane and diborane.

TABLE 2

Reduction Oxidation Reactions of Hydride Gases with Copper (II) Oxide.

| Redox Reactions | $\Delta$g/mol | $e°(V)$ |
|---|---|---|
| $3CuO + 2AsH_3(g) \rightarrow 3Cu + 2As + 3H_2O\uparrow$ | 102.0 | 0.95 |
| $3CuO + 2PH_3(g) \rightarrow 3Cu + 2P + 3H_2O\uparrow$ | −14.0 | 0.45 |
| $2CuO + SiH_4(g) \rightarrow 2Cu + Si + 2H_2O\uparrow$ | −3.9 | favorable |
| $3CuO + B_2H_6(g) \rightarrow 3Cu + 2B + 3H_2O\uparrow$ | −26 | favorable |

Reactions with hydride gas of a piezoelectric crystal coated with copper(II) nitrate- or copper(II) oxide-containing inert porous coatings, while useful to detect the presence of hydride gases, have a lower sensitivity to arsine compared to silver(I) nitrate. Such difference may be due to the smaller change in mass loading after reaction with arsine, the lower reduction potential and/or slower kinetics of the reaction. In general, higher sensitivity of the reactive sensor material in the inert coating is desired over lower sensitivity reactive sensor materials.

Similar sol gel techniques may be employed to prepare coatings to detect other gas types, for example acid gases. Acid gas sensors of the invention may be utilized in semiconductor manufacturing process systems in which ion implantation using boron trifluoride ($BF_3$) is employed. $BF_3$ upon exposure to air forms hydrogen fluoride (HF). Etch processes may also be employed in such semiconductor manufacturing process systems using chlorine and boron trichloride which form hydrogen chloride upon exposure to air. A metal salt for the active metal species is utilized in the sol gel process which is soluble in the solvent medium employed to form the sol gel solution, and such metal salt is selected to provide suitable mass change characteristics upon reaction with the fluid component of interest (in the gas being monitored or subjected to detection by the sensor). In such acid gas sensing applications, calcium iodide is an illustrative potentially useful candidate as the active metal species of the sensor material on the piezoelectric crystal. Calcium iodide is soluble in both water and alcohol, and reacts favorably with both hydrogen fluoride and hydrogen chloride. The equilibrium constants of the reactions of $CaI_2$ with HF and HCl and the weight changes associated with the reaction are shown in Table Three. Such data are consistent with the viability of calcium iodide as an active metal species for the sensor with dependencies on temperature, flow and moisture.

TABLE 3

Reaction chemistry of calcium iodide with acid gases.

| Reaction | $\Delta$g/mol | $K_{eq}$ |
|---|---|---|
| $CaI_2 + 2HF \rightarrow CaF_2 + 2HI$ | −216 | $10^{16}$ |
| $CaI_2 + 2HCl \rightarrow CaCl_2 + 2HI$ | −183 | $10^4$ |

In the formation of the sensor element of the invention, the loading of the metal species in the inert porous material coating on the piezoelectric crystal may be widely varied, within the skill of the art, to provide a suitable loading with the desired frequency response characteristics for the specific end use application contemplated.

The moisture concentration in the fluid stream and the temperature of the fluid being monitored affects the sensor response. In order to predict actual concentrations of the monitored or sensed gas component, the humidity and temperature of the gas stream or other fluid medium being monitored or sensed, is desirably measured, and the temperature of the fluid medium is appropriately controlled. The operating equation for response of the sensor includes a concentration of toxic gas (sensed fluid component) term, a flow rate term, and a water term, with additional noise terms for pressure and temperature. The general form of the equation is:

Response (Hz/min/ppm/sccm)=$A$[Hydride](Flow Rate) $(b-e^{b[H_2O]-1})+dP/dt+d°C./dt$ where:

A=constant

[Hydride]=toxic gas (sensed fluid component) concentration in ppm flow rate=total flow of the gas stream b=constant

[$H_2O$]=humidity in ppm

P=pressure

°C.=temperature in °C.

t=time in minutes

In the sensor apparatus of the invention, an additional piezoelectric crystal may be employed in the sensor assembly as a reference crystal. This reference crystal desirably does not react with the toxic gas (sensed fluid component) but has the same fluctuations due to temperature and pressure as the sensing crystal. Such provision of an extra crystal will remove some of the noise elements in the above equation.

In the practice of the invention, particulates should be kept away from the sensor element, in order to avoid false alarms due to additional loading of the particulates on the crystal.

To maintain a constant flow of the sensed fluid medium to the sensor element and to avoid contamination of the sensor element with particulates, a frit or a flow restrictor may be deployed in a gas flow passage, e.g, conduit, through which the gas being sampled is flowed. Such flow restriction means may be employed to force the flow to be purely or substantially diffusional in character, and it will act as a particle filter at the same time. Such a flow restrictor device may be interposed for example between a conduit whose end is joined to the sensor housing and a conduit whose end is joined to the manifold of the scrubber bed assembly.

The flow restrictor may in a specific embodiment comprise a ¼" Teflon® plug in a KF25 tee which has a single ⁵⁄₁₆"–18 tapped hole in it to allow diffusion of the gas to the sensor. The single hole will provide enough medium for gas to diffuse through without clogging.

If there are many particulates in the gas stream, then in place of such a single hole flow restrictor, a porous frit may alternatively be utilized.

In some instances, the gas being monitored for the presence of a specific hydride may contain other hydride species, or more generally, the coating material used in the sensor may be chemically reactive with a number of species in the gas. In such instances, it may be necessary to provide ancillary treatment of the gas to remove the species thereof which are not of interest in the monitoring or detection process.

For example, if the specific sensor is not selective for hydride gas of a specific type, but rather responds similarly to all three chloride gases in a gas containing same which is undergoing scrubbing treatment, then it may be desirable to install a guard column or other extraneous halide gas removal means, upstream of the sensor receiving the gas being monitored.

In the broad practice of the present invention, sensor coatings with oxidizing characteristics may be utilized to detect hydride gases. For example, oxidation of a Cu, Cr, or Ag metal species to the corresponding oxide salt may be carried out for such purpose. Such oxides react with the hydrides to form non-volatile salts (and hydrogen/water). There is a net change in weight (relative to the starting sensor coating material) when such reaction occurs. Mass-sensitive piezoelectric sensors can be used to readily and economically detect the occurrence of such reaction:

$3CuO+2AsH_3 \rightarrow Cu_3As_2+3H_2O$

The sensor device of the present invention may be readily fabricated and deployed to provide accurate and reliable sensing of impurity species of interest in gas scrubbing applications of the type wherein a solid scavenger or chemisorbent material having removal capability for the impurity is contacted with the gas to remove the impurity therefrom, and wherein the sensor is utilized to determine the presence of breakthrough and/or leakage of the impurity from the bed or beds in the scrubbing system.

The gas sensor of the present invention also has utility for environmental monitoring applications in which the coated piezoelectric crystal is provided to sense the presence of undesired components in a fluid environment such as air or other ambient gases.

FIG. 1 is a schematic view of a dry scrubber system featuring a piezoelectric crystal sensor assembly according to one embodiment of the invention. This process system comprises a scrubber vessel 20 containing a quantity of a dry scrubber material 22 as a bed or mass in the vessel. The dry scrubber vessel 20 is arranged in receiving relationship to the process facility 24, which discharges a waste gas in line 26. The waste gas stream containing the impurity to be scrubbed from the gas enters the dry scrubber vessel in line 26 for scrubbing therein to deplete the gas of scrubbed component.

The dry scrubber vessel 20 has a vertically upstanding discharge conduit 28 disposed in the interior volume of the scrubber vessel, with its lower end open to receive scrubbed gas for flow upward in the conduit 28 and discharge therefrom at the open upper end of the conduit in the direction indicated by arrow M. The open upper end of the conduit 28, terminating exteriorly of the scrubber vessel 20, may be arranged to discharge the scrubbed gas to an exhaust means of the process facility, or otherwise such conduit at its open upper end may be joined to other flow passage means or apparatus for further treatment and/or disposition of the scrubbed gas.

The dry scrubber vessel 20 also has disposed therein and terminating exteriorly thereof a sampling conduit 30 receiving scrubbed gas at its open lower end for flow upwardly therein. Exterior of the scrubber vessel 20, a guard bed 32 is provided in conduit 30 for removing from the scrubbed gas stream any extraneous impurities which may react with the reactive metal species in the inert porous coating on the piezoelectric sensor 36, and thereby adversely affect the sensor's accuracy for the impurity species of interest.

The guard bed may therefore contain a chemisorbent scavenger for the extraneous impurity species, so that the sample gas stream in conduit 39 is passed to the piezoelectric sensor depleted in such extraneous fluid component(s). Intermediate the guard bed 32 and the piezoelectric sensor 36 is an optional flow restrictor 34, which may for example be of the type previously described, for the purpose of maintaining the flow rate of the sample gas passed to the piezoelectric sensor at a level consistent with good operating life characteristics of the sensor.

As an alternative flow restricting feature, the diameter of the conduit 30 may be significantly less than the diameter of conduit 28, so that the side stream in conduit 30 is correspondingly only a portion of the flow discharged from the vessel 20 in conduit 28.

As a still further alternative flow restricting feature, the conduit 30 may with the conduit 48 downstream of the guard bed 32, form a main flow passage for discharge of scrubbed gas from the scrubber vessel (in lieu of, or in addition to, the conduit 28), and the conduit 39 may be provided with appropriate dimensions to attenuate the flow of gas to the piezoelectric sensor 36. For example, the conduit 39 may have a diameter which is smaller than the diameter of conduits 30 and 48, or alternatively, the conduit 39 may simply by virtue of its length from the junction with conduit 48 to the sensor 36 serve to diminish the flux of the sampled scrubbed gas to an appropriate level.

Thus, the main flow of scrubbed gas from the scrubber vessel may be substantial, e.g., 40 liters per minute or more, and such gas flow would if directly contacted with the sensor coating rapidly deplete the coating even at low trace levels of the impurity, due to the cumulative large volume which would be experienced by the coating.

Accordingly, it is desired in the practice of the present invention to restrict the flux of the sampled gas stream to the sensor such that the coated piezoelectric crystal exhibits a frequency response rate to the trace fluid component in the range of from about 0.001 to about 100,000 milliHertz/min/(part-per-million of the fluid component), preferably in the range of from about 0.01 to about 10,000 milliHertz/min/(part-per-million of the fluid component), more preferably in the range of from about 0.1 to about 5,000 milliHertz/min/(part-per-million of the fluid component), and most preferably in the range of from about 1 to about 1000 milliHertz/min/(part-per-million of the fluid component). Such arrangement may as previously described entail the sampling by the coated piezoelectric crystal of a slip-stream or side-stream of a main flow of process fluid, or the restricted access of the main flow of fluid to the coated piezoelectric crystal.

The sampled gas stream after contact with the coating on the piezoelectric sensor is discharged from the sensor 36 in line 44, from which the sampled gas may be recycled to the main gas stream, or otherwise disposed of in the process facility.

As shown in FIG. 1, the piezoelectric sensor 36 comprising coated crystal 38 is operatively coupled, e.g., by signal transmission lines 40 and 41, to electronics module 42.

The electronics module includes suitable output means, e.g., comprising a liquid crystal display (not shown), which may numerically display a concentration value or other information for the impurity gas being monitored. Alternatively, the output means may provide a colorimetric display, e.g., with red indicating a hazardous or dangerously high concentration of the gas component of interest, yellow indicating a tolerable but high concentration of the gas component, and green indicating that the gas component concentration is within acceptable concentration limits. As still other alternatives, the output means may comprise a audible alarm, other visual display (e.g., a flashing light), or any other suitable output means.

The electronics module 42 is constructed and arranged for (i) sampling the output resonant frequency of the piezoelectric crystal while the oscillating electric field is applied thereto, (ii) determining the change in resonant frequency from the fundamental resonant frequency that occurs on formation of the solid interaction product when the sensor material interacts with the trace fluid component in the sampled fluid stream, and (iii) generating an output indicative of the presence of the trace fluid component in the fluid stream, with the coated piezoelectric crystal exhibiting a frequency response rate to the trace fluid component in the range of from about 0.001 to about 1000 milliHertz/min/(part-per-million of the fluid component).

Figure 2:
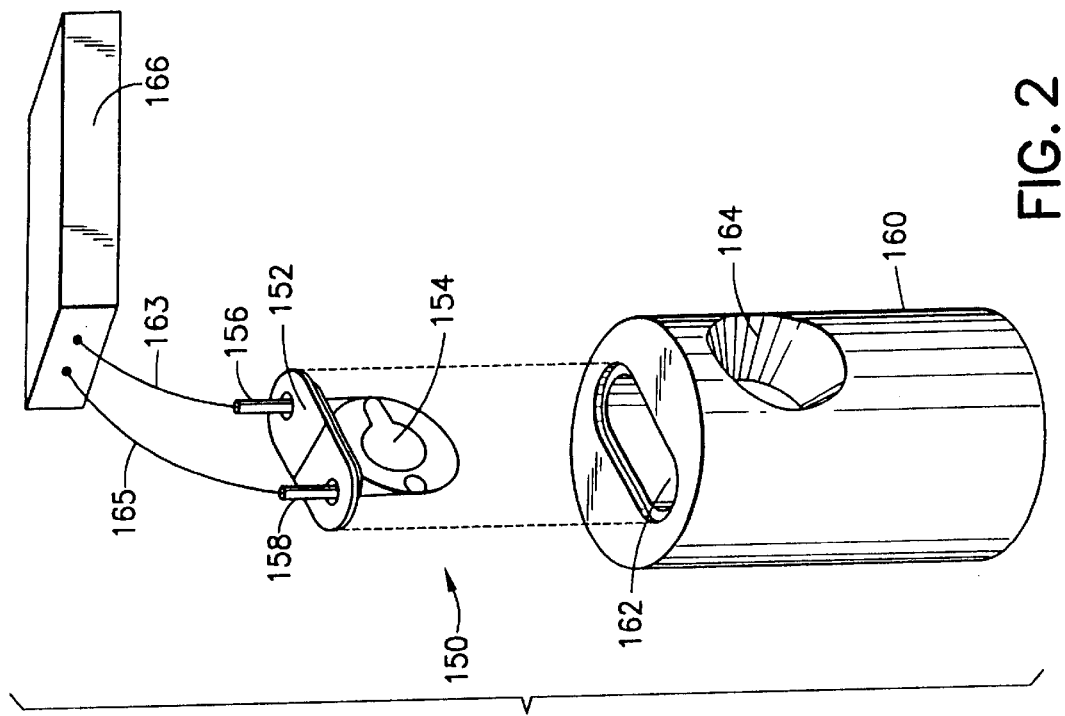
FIG. 2 is a sensor assembly for a process system or an environmental monitor, according to another embodiment of the invention.

FIG. 2 shows an exploded view of a sensor assembly according to another embodiment of the invention, comprising the sensor element 150 and the housing 160. The sensor element 150 comprises the piezoelectric crystal 154 which is coated with a suitable inert porous material containing a metal species material interacting with the fluid component of interest to yield an interaction product of differing mass characteristic than the original coating material. The coated crystal is mounted on the plug member 152, with the respective leads of the piezoelectric crystal 154 protruding exteriorly of the plug member when the plug member is engaged with the housing 160 with the coated crystal extending into the cavity 162.

The housing 160 features an opening 164 by which a gas can be flowed into the cavity 162 containing the sensor element 150. Although not shown in the front perspective view of FIG. 2, the housing 160 has another opening therein, opposite opening 164 and in register with such opening, for discharge from the housing of the gas flowed past the coated piezoelectric crystal.

The leads 156 and 158 of the sensor element may be coupled in circuit relationship to suitable electronics means shown schematically as electronics module 166 in FIG. 2, by which the presence and concentration of the gas impurity species can be detected. The electronics module 166 is coupled to the sensor element leads 156 and 158 by wires 163 and 165, respectively.

Electronics module 166 provides the functions of (i) sampling the output resonant frequency of the piezoelectric crystal while the oscillating electric field is applied thereto, (ii) determining the change in resonant frequency from the fundamental resonant frequency incident to the formation of the solid interaction product when the sensor material interacts with the trace fluid component in the fluid being monitored, and (iii) generating an output indicative of the presence of the trace fluid component in such fluid.

In a specific embodiment of the sensor assembly shown in FIG. 2, the housing 160 may comprise an aluminum housing which has the cavity 162 machined into it for insertion of the sensor element, as well as two feedthrough (¼" NPT) openings (opening 162 and the opposite opening not shown in FIG. 3) for the gas to flow through the sensor. In the body of this housing is the flow restricting orifice. This ¼" aluminum housing fits directly on the scrubber vessel and the front end driver electronics are plugged directly onto the legs (leads 156 and 158) of the sensor assembly. The resulting assembly may be coupled to a sensor tube of the scrubber vessel, or otherwise joined in flow sensing communication with the scrubber vessel or scrubber bed therein.

Figure 3:
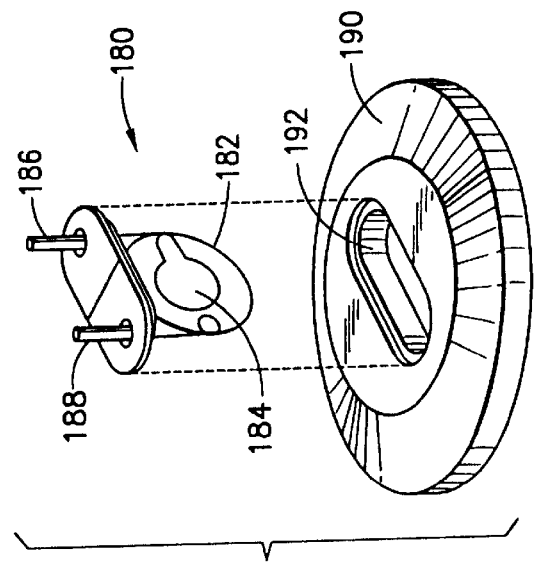
FIG. 3 is a sensor assembly for a process system or an environmental monitor, according to yet another embodiment of the invention.

FIG. 3 is an exploded perspective view of another sensor assembly according to the present invention, comprising the sensor element 180 and the receiving fitting 190. The sensor element 180 comprises the piezoelectric crystal 182 which is coated with an inert porous material coating containing a suitable metal species material interacting with the fluid component of interest to yield an interaction product of differing mass characteristic than the original coating material. The coated crystal is mounted on the plug member 184, with the respective leads 186 and 188 of the piezoelectric crystal protruding exteriorly of the plug member when the plug member is engaged with the receiving fitting 190 with the coated crystal extending into the cavity 192.

In a specific embodiment, the receiving fitting comprises a KF25 blank which will fit into a KF25 tee having a flow restricting orifice in the same leg as the sensor. The electronics associated with the sensor element plug directly into the legs of the sensor unit (leads 186 and 188).

It will be appreciated that the sensor device of the invention may assume a wide variety of conformations and arrangements in the broad practice of the invention, consistent with the specific end use of the sensor device, and the nature and extent of the output function thereof.

The features and advantages of the invention are more fully illustrated by the following non-limiting examples, wherein all parts and percentages are by weight, unless otherwise expressly stated.

EXAMPLE 1

Figure 4:
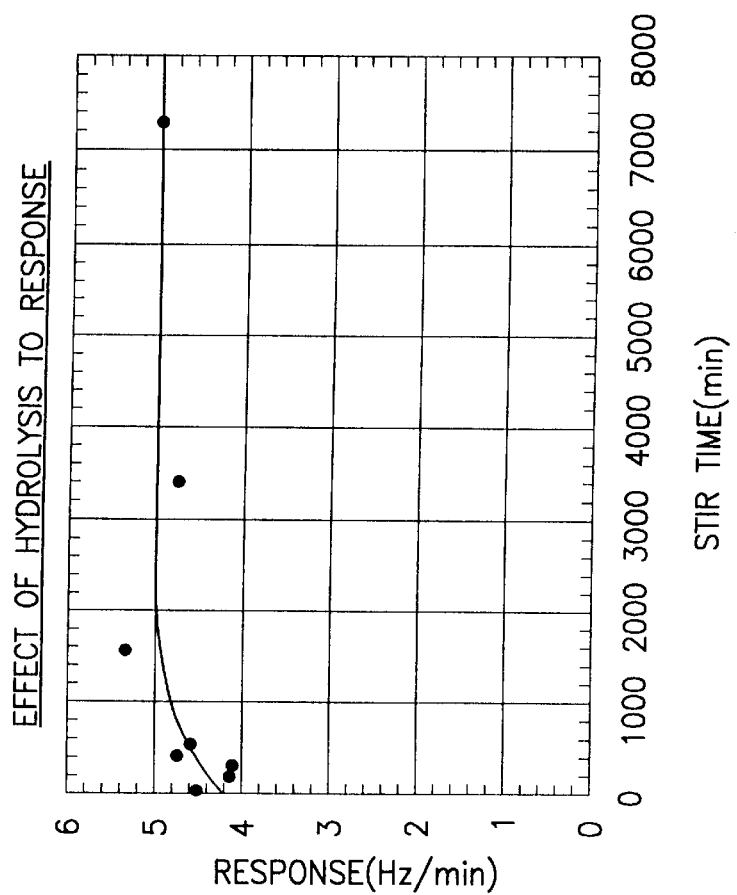
FIG. 4 is a graph showing silver nitrate sensor material response to arsine as a function of hydrolysis time.

Tetraethylorthosilicate (TEOS) was mixed in methanol with silver nitrate in water and acid catalyzed to form a sol. The mol ratio of components in such sol gel formulation was $AgNO_3:H_2O:TEOS=10:45:1$. $AgNO_3$ was dissolved in water in one vial, and TEOS and methanol were mixed together in another vial. Once the $AgNO_3$ was completely dissolved, it was added to the TEOS/MeOH solution. A white precipitate was formed. Three milliliters of nitric acid were added to dissolve the precipitate and acid catalyze the hydrolysis reaction. The solution was maintained under stirring conditions for at least 18 hours. The viscosity of the resulting composition was 1.5 centipoise at 23° C. The weight % of the $AgNO_3$ and TEOS was 20% in the water/methanol medium. The length of time the solution is allowed to hydrolyze is related to the sensitivity of the final coating. The length of time necessary to consistently form a coating with the required sensitivity was determined. A graph of the sensor response vs. hydrolysis time is shown in FIG. 4. The optimum hydrolysis time for this specific formulation as shown in the graph is 2000 minutes (33 hours). Based on the deviation in response after that point a 1000 minute or 18 hour hydrolysis period should be acceptable as well. Since the response does not vary significantly between 18 hours and the length of the test, multiple crystals may be coated from the same batch of sol gel solution without variance in response.

EXAMPLE 2

Figure 5:
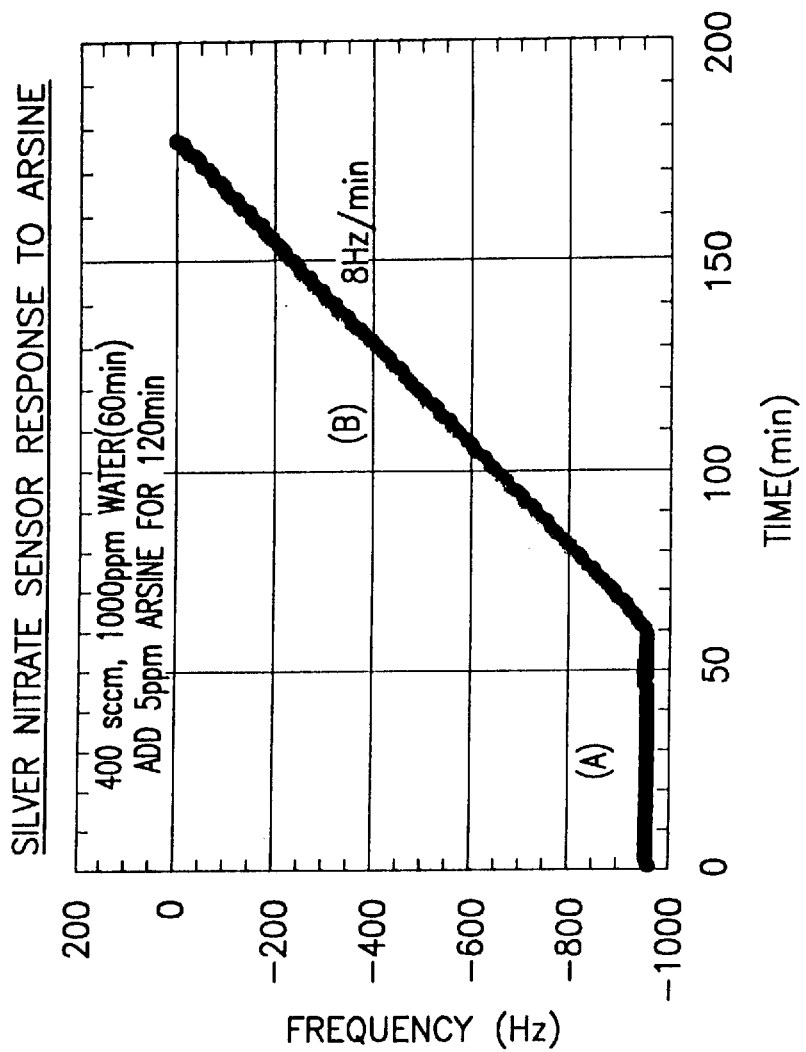
FIG. 5 is a graph showing the response of a sensor according to the invention, utilizing silver nitrate as the reactive metal species, in exposure to arsine.

FIG. 5 shows the response curve of an activated piezoelectric crystal in exposure to arsine. The x axis represents the time in minutes and the y axis represents the frequency response, in Hz. The curve has been normalized to zero Hz. There are two stages in the response curve. The first portion (A) is linear because the sensor was exposed to a constant flow of wet nitrogen with no arsine. After 60 minutes, arsine was added to the gas stream causing the sensor response slope to immediately rise (B). The frequency is increasing because there was a net decrease in the mass loading on the crystal in the transformation of silver nitrate to silver arsenide due to loss of nitric acid.

The sensor response of 8 Hz/min. at 5 ppm translates to a response of 0.08 Hz/min. at TLV. Electronics can be provided to measure as low as 0.009 Hz/min., therefore enabling detection of concentrations as low as 17 ppb arsine. This particular sensor response remained linear for 1450 Hz at 5 ppm arsine (8 Hz/min. response). This translates to approximately 12.6 days of lifetime at 50 ppb arsine (TLV). By contrast, a current monitoring system will last approximately 8 hours with constant exposure to TLV concentrations of arsine.

EXAMPLE 3

Figure 6:
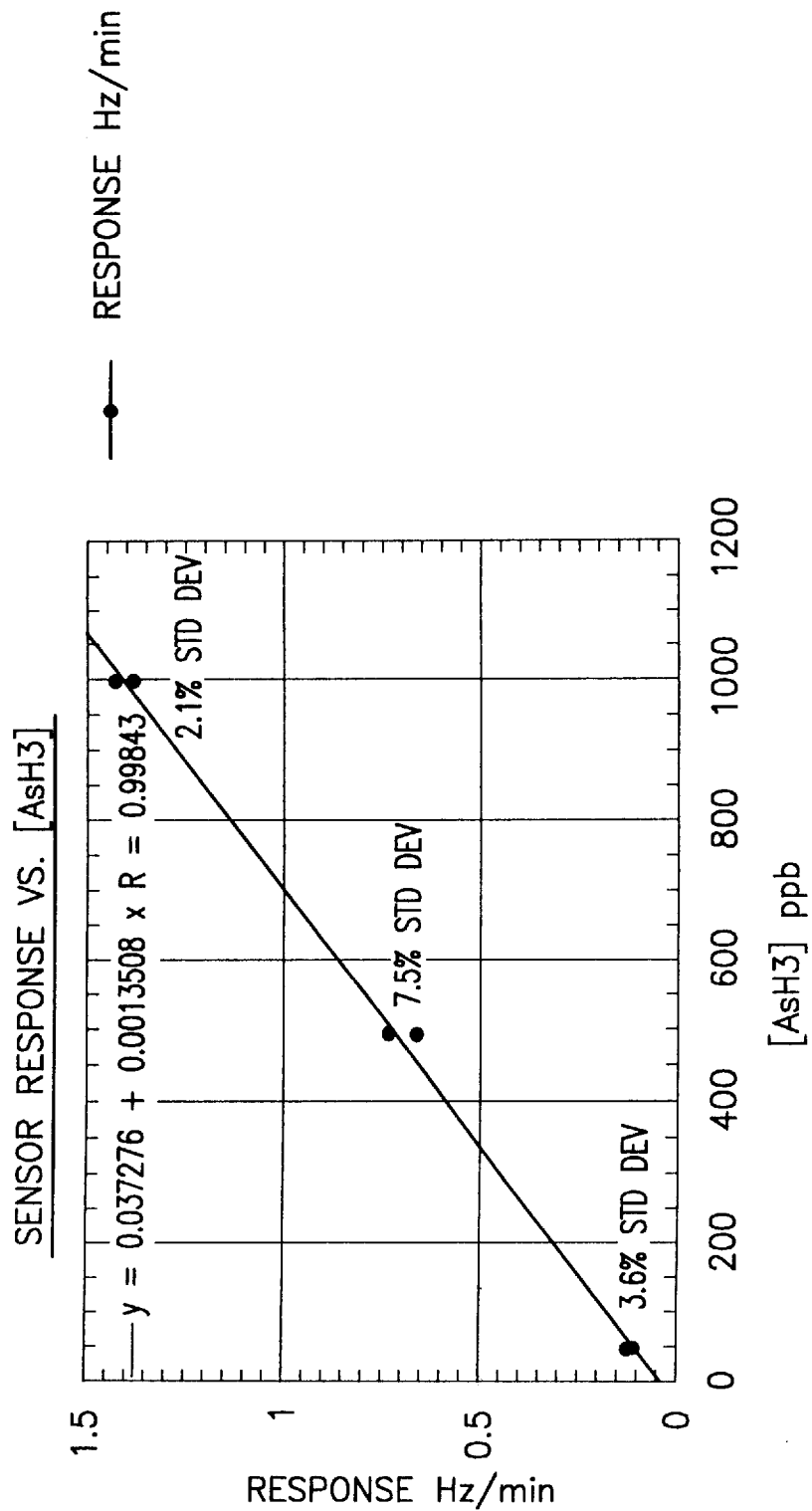
FIG. 6 is a graph showing the response of a sensor according to the invention, utilizing silver nitrate as the reactive metal species, in exposure to arsine, as a function of arsine concentration.

The sensor response signal must be linear and have immediate response to enable development of a linear output proportional to the concentration of toxic gas. A single sensor was tested at varying concentrations of arsine to show that the sensor responded linearly to variations in gas concentrations at the concentration range of interest. The results are shown in FIG. 6. The sensor responds at concentrations as low as 50 ppb arsine.

EXAMPLE 4

Figure 7:
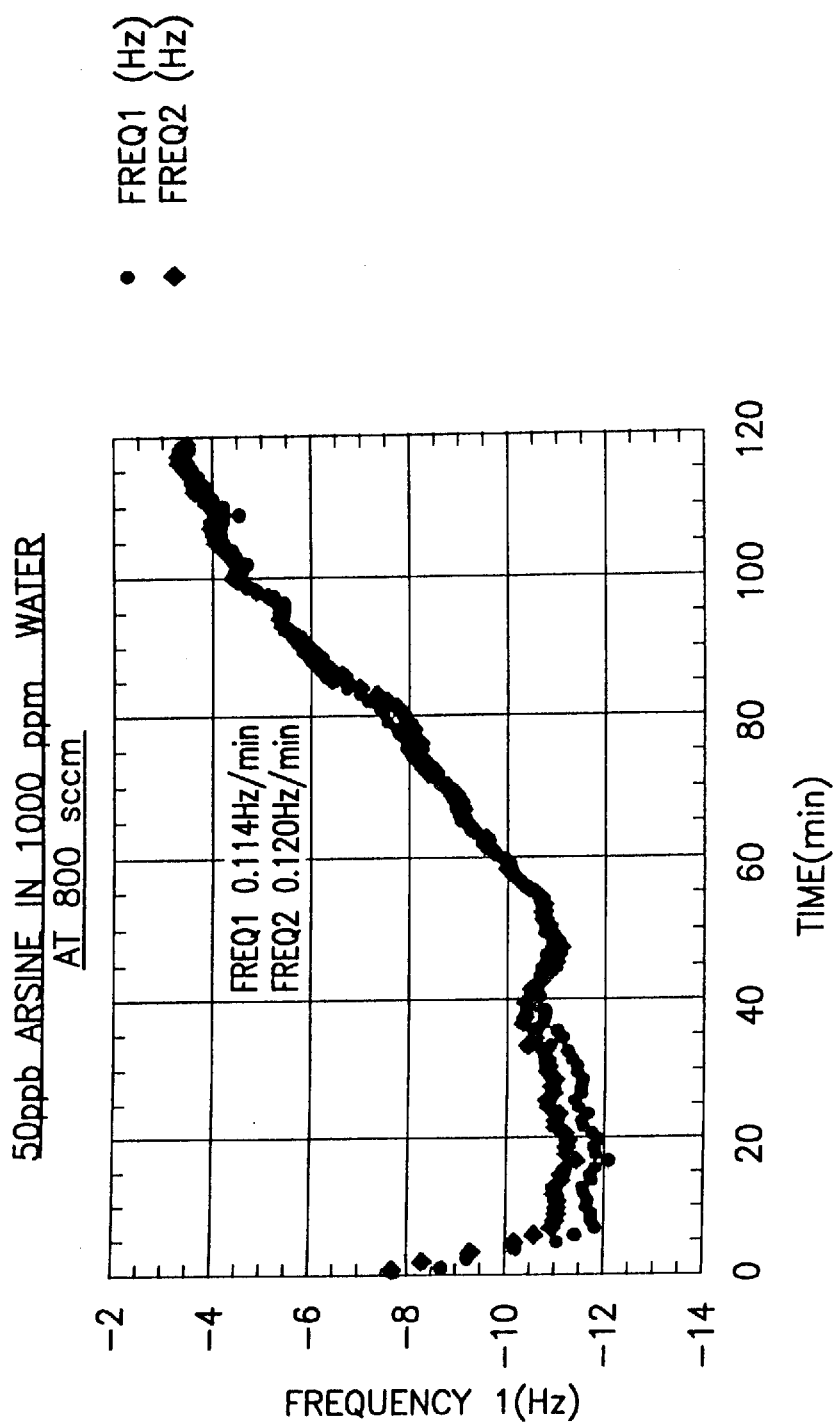
FIG. 7 is a graph showing the response of a sensor according to the invention, utilizing silver nitrate as the reactive metal species, in exposure to arsine at 50 ppb $AsH_3$.

A sensor prepared in accordance with the procedure of Example 1 was tested to demonstrate that it will respond at a measurable rate to 50 ppb arsine. The raw data recorded pertaining to the sensor response at TLV of arsine is shown in FIG. 7. This graph has two stages to it, viz., stage one from 0 to 44 minutes, and stage two where arsine was added to the system from 45 minutes to the end of the experiment. In stage one the sensor was exposed to a constant concentration of wet nitrogen and was allowed to equilibrate to this water concentration and flow rate. The initial dip in the frequency was due to the wetting of the sensor which caused an increase in the mass on the crystal therefore reducing the frequency. At 45 minutes when 50 ppb of arsine was added to the gas stream the frequency increased due to the reduction in mass of the crystal. This was a direct result of the reaction of silver nitrate with arsine to form silver metal, arsenic and nitric acid. In the reaction, it appears that the arsenic replaces the nitric acid on the crystal, which results in a net loss in mass on the crystal thereby increasing the frequency.

EXAMPLE 5

Figure 8:
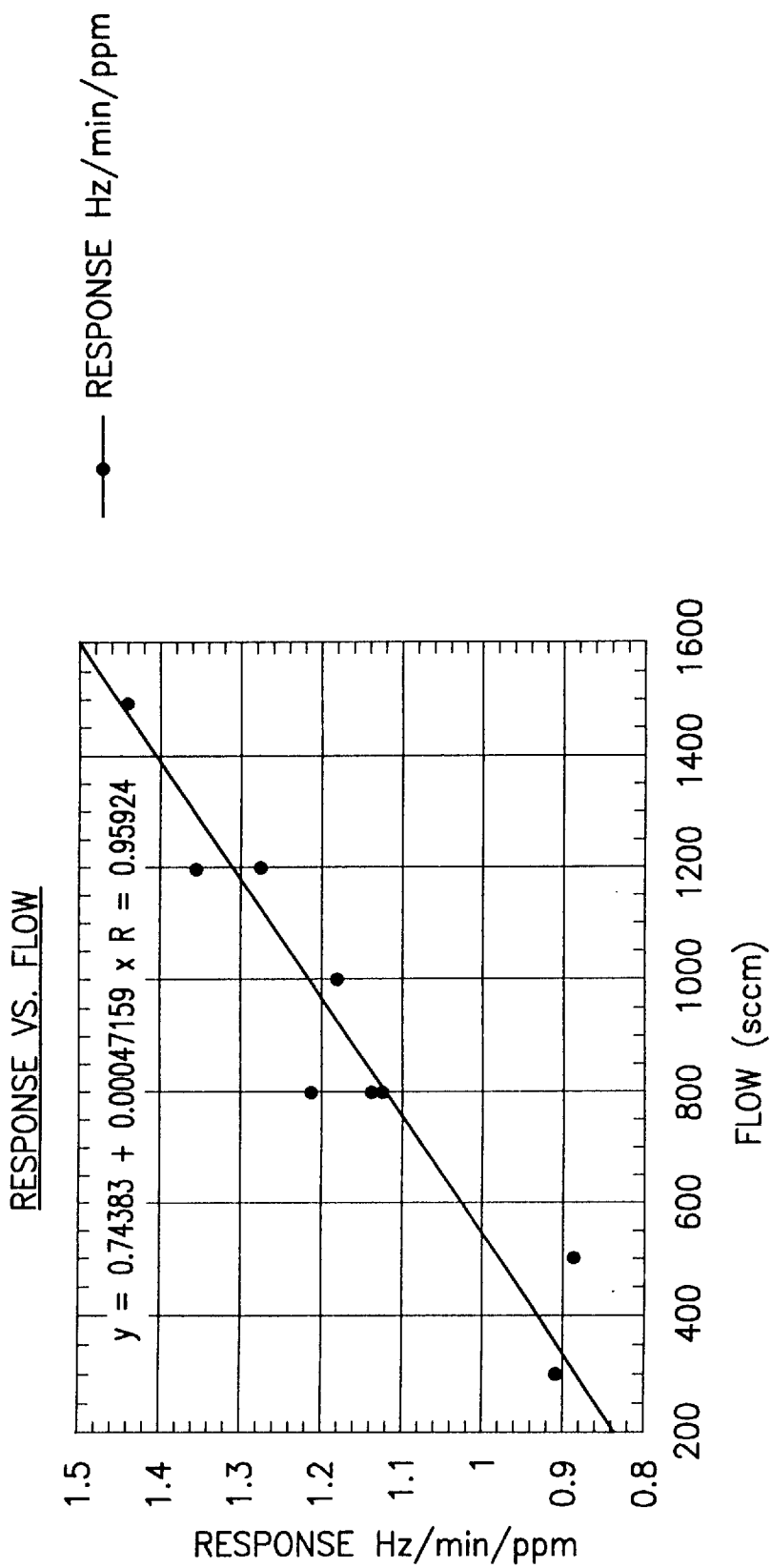
FIG. 8 is a graph showing the response of a sensor according to the invention, utilizing silver nitrate as the reactive metal species, in exposure to arsine, as a function of the total gas flow.

FIG. 8 shows data for the sensor response to arsine, with varying flows from 200 sccms to 1500 sccms. The data shows that a useful operating flow range for environmental monitoring applications is on the order of 1000 sccms.

EXAMPLE 6

Figure 9:
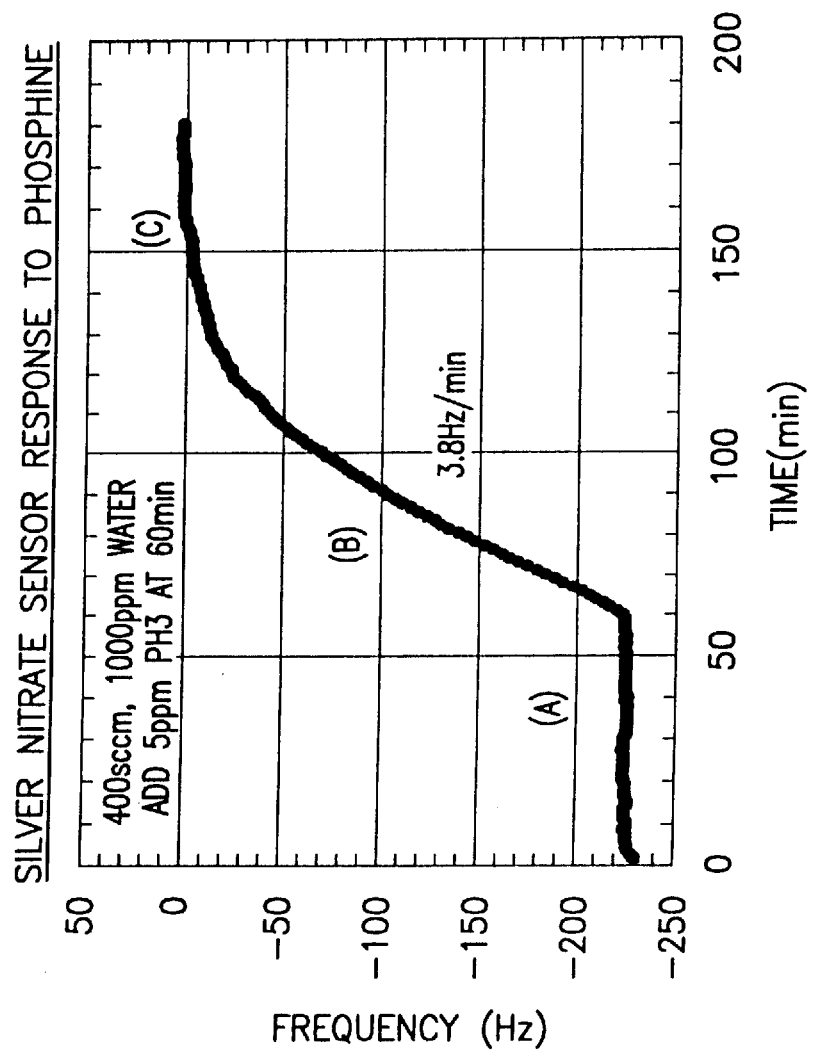
FIG. 9 is a graph showing the response of a sensor according to the invention, utilizing silver nitrate as the reactive metal species, in exposure to phosphine.

The sensor coating of Example 1 was tested to detect phosphine, shown in FIG. 9. In this experiment, phosphine was flowed past a silver nitrate-containing coated quartz microbalance. Section (A) of the graph indicates the period in which the sensor stabilizes to a constant water concentration. Section (B) is the period in which phosphine was added to the gas stream at a 5 ppm (TLV=0.5 ppm). The response is 3.816 Hz/min. at 5 ppm which is predictive of 0.3816 Hz/min. at TLV. In this system a change of 0.009 Hz/min is detectable. Section (C) indicates a flattening of the sensor response. The sensor has a limited lifetime at this high concentration of phosphine. At 0.3816 Hz/min. phosphine this sensor will last over eight hours (or one full shift) at constant exposure to TLV concentrations of phosphine.

EXAMPLE 7

Figure 10:
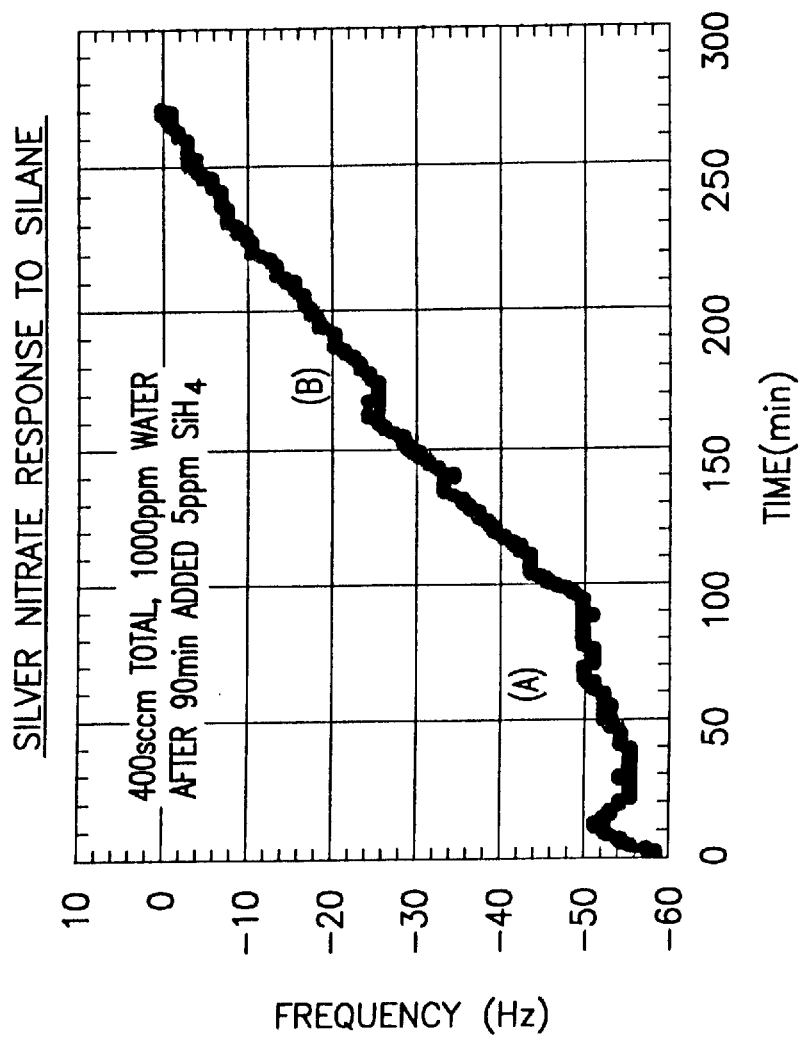
FIG. 10 is a graph showing the response of a sensor according to the invention, utilizing silver nitrate as the reactive metal species, in exposure to silane.
Figure 11:
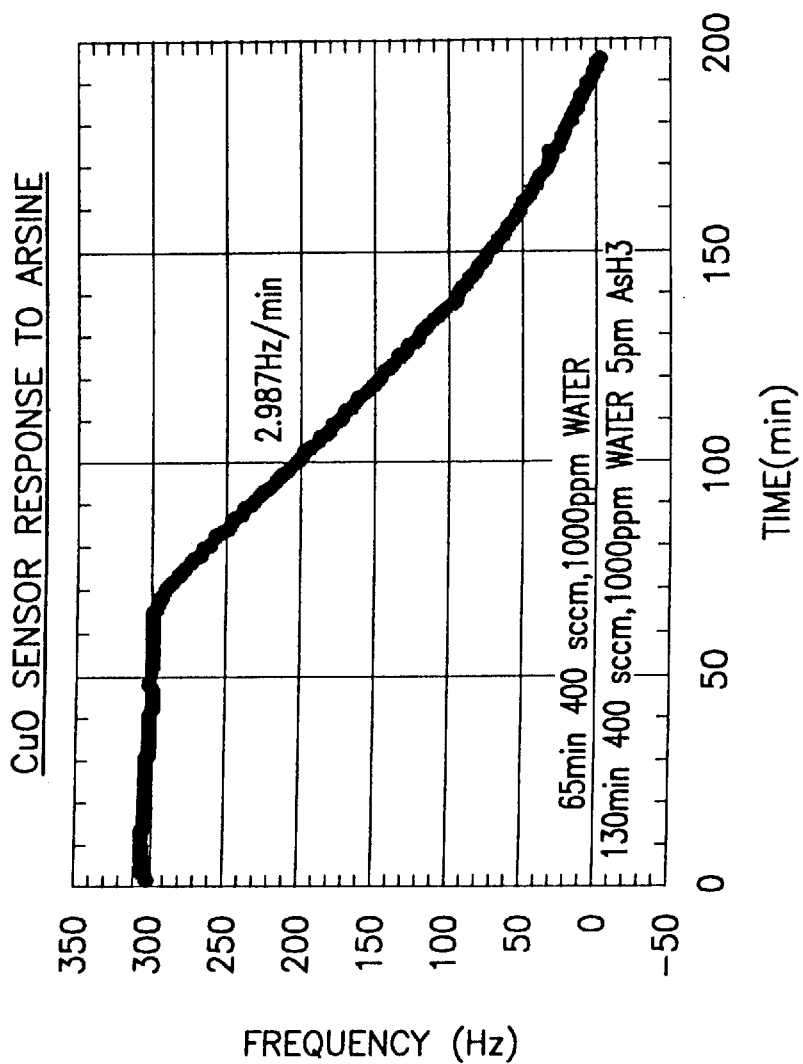
FIG. 11 is a graph showing the response of a sensor according to the invention, utilizing copper(II) oxide as the reactive metal species, in exposure to arsine.
Figure 12:
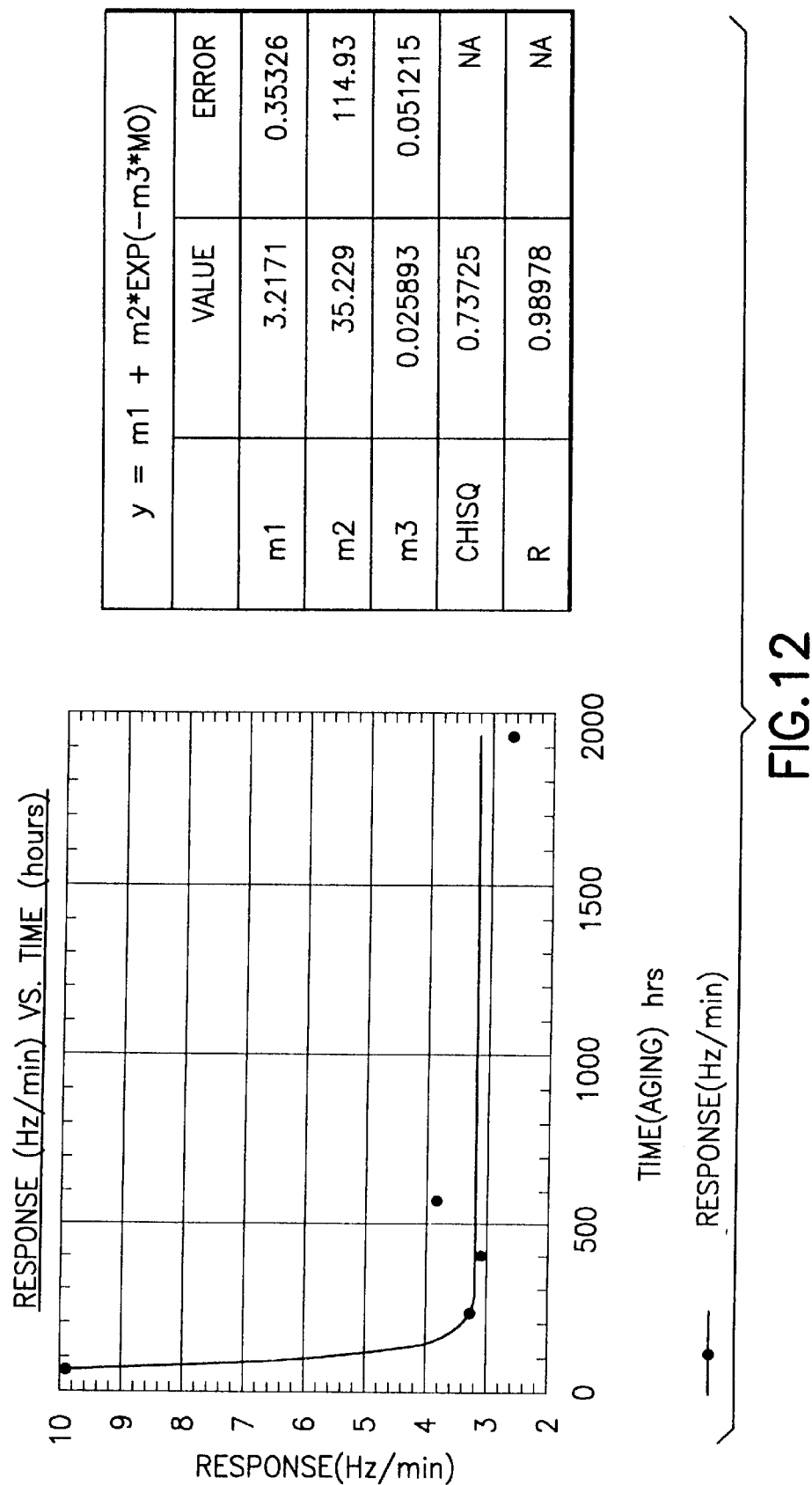
FIG. 12 is a graph showing the response of a sensor according to the invention, utilizing silver nitrate as the reactive metal species, in exposure to arsine, as a function of storage time.

The sensor coating of Example 1 was used to detect silane. The data are shown in FIG. 10. This data are the result of flowing silane past a silver nitrate-containing sol gel coated quartz microbalance. Section (A) of the graph indicates the period in which the sensor stabilized to a constant water concentration. Section (B) indicates the period in which silane was added to the gas stream at a concentration equivalent to TLV (5 ppm). The response is 0.278 Hz/min. As previously stated, the detectable response for this system for is 0.009 Hz/min.

EXAMPLE 8

The main requirement of the reactive coating material in the sensor is that it contains a species which will react with the trace fluid component of interest at a measurable rate and that it will have a sufficient lifetime. The types of coatings which are preferred are ones with substantial surface area which contain a metal which is easily reduced. An example of such a coating is a silicate matrix containing CuO. In this example, a sensor was coated with a sol gel matrix containing CuO and the response was recorded.

A typical response curve of a sensor crystal coated with a porous material containing CuO and then exposed to arsine is shown in FIG. 11. The x axis is time in minutes and the y axis is frequency in Hz which has been normalized to zero Hz. The frequency response after addition of arsine immediately decreased as expected because of the net increase in mass on the sensor due to the reaction of CuO with arsine.

EXAMPLE 9

Coating procedures utilizing the sol gel method must take into account rearrangement of the sol gel over time, in the binder ($SiO_2$) prepared by the polymerization process. It has been found with the silver nitrate sol gel matrix that the sensor response changes significantly during the first 10 days after coating but remains essentially constant after that point, as shown in FIG. 12. The coating was aged and tested for approximately three months. The time period in which the sensor varied in response was when the gel was drying to form the xerogel. The amount of time required to dry the sensor can vary depending on the temperature in which the crystal is stored. If temperature is elevated to reduce the aging period, then the properties of the sensor may change depending on the temperature of the storage.

While the invention has been described herein with reference to specific aspects, features, and embodiments, it will be apparent that other variations, modifications, and embodiments are possible, and all such variations, modifications, and embodiments therefore are to be regarded as being within the spirit and scope of the invention.

What is claimed is:

1. A sensor element for detection of a trace fluid component in a fluid environment, comprising:

a piezoelectric crystal having a fundamental resonant frequency in response to an applied oscillating electric field; and an inert porous material coating on the piezoelectric crystal to provide a coated piezoelectric crystal, the coating containing a metal species which is reactive with the trace fluid component to yield a solid interaction product of changed mass in relation to an initial mass of the metal species interacting with the trace fluid component to yield the solid interaction product, the coated piezoelectric crystal exhibiting a frequency response rate to the trace fluid component in the range of from about 0.001 to about 100,000 milliHertz/min/(part-per-million of the fluid component);

wherein the sensor element is constructed and arranged to measure the differential frequency rate of change, dF/dt.

2. A sensor element according to claim 1, wherein the piezoelectric crystal comprises a piezoelectric silica crystal.

3. A sensor element according to claim 1, wherein the coated piezoelectric crystal exhibits a frequency response rate to the trace fluid component in the range of from about 1 to about 5000 milliHertz/min/(part-per-million of the fluid component).

4. A sensor element according to claim 1, wherein the piezoelectric crystal has a fundamental resonant frequency in the range of from 1 Megahertz to 20 Megahertz.

5. A sensor element according to claim 1, wherein the metal species comprises a metal oxide or a metal salt which is reducible by the trace fluid component comprising a hydride gas.

6. A sensor element according to claim 1, wherein the metal species includes a metal oxide or metal salt whose metal moiety is selected from the group consisting of copper, zinc, calcium, silver, manganese, sodium, iron and chromium.

7. A sensor for detection of a trace fluid component in a fluid environment, comprising:

a piezoelectric crystal having a fundamental resonant frequency in response to an applied oscillating electric field;

an inert porous material coating on the piezoelectric crystal containing a metal species which is reactive with the trace fluid component to yield a solid interaction product of changed mass in relation to initial mass of the metal species interacting with the trace fluid component to yield the solid interaction product;

means for applying an oscillating electric field to the piezoelectric crystal which generates an output resonant frequency therefrom;

means for (i) sampling the output resonant frequency of the piezoelectric crystal while the oscillating electric field is applied thereto, (ii) determining the differential frequency rate of change in resonant frequency over time from the fundamental resonant frequency that occurs on formation of the solid interaction product when the metal species material interacts with the trace fluid component in the fluid environment, and (iii) generating an output indicative of the presence of the trace fluid component in the environment; and means for flowing fluid from the fluid environment to the coating on the piezoelectric crystal so that the trace fluid component when present reacts with the metal species material to form the solid interaction product;

wherein the coated piezoelectric crystal exhibits a frequency response rate to the trace fluid component in the range of from about 0.001 to about 1000 milliHertz/min/(part-per-million of the fluid component).

8. A sensor according to claim 7, wherein the means for (i) sampling the output resonant frequency of the piezoelectric crystal while the oscillating electric field is applied thereto, (ii) determining the change in resonant frequency from the fundamental resonant frequency that occurs on formation of the solid interaction product when the metal species material interacts with the trace fluid component in the fluid environment, and (iii) generating an output indicative of the presence of the trace fluid component in the environment, comprises a circuit including therein a frequency counter.

9. A sensor according to claim 7, wherein said output indicative of the presence of the trace fluid component in said environment, comprises a calculated concentration of said trace fluid component in said environment.

10. A sensor according to claim 9, further comprising a flow control means for controllably flowing a selected flow rate of fluid of said fluid environment in contact with the metal species on said piezoelectric crystal, and wherein the means for performing functions (i), (ii) and (iii), comprise computational means for determining said calculated concentration of said trace fluid component in the fluid environment.

11. A sensor according to claim 7, further comprising a flow passage accommodating flow therethrough of fluid of the fluid environment, and having a diffusional flow restrictor in the passage, arranged in relation to the metal species to permit substantially only diffusional flow from the flow passage through the diffusional flow restrictor to the metal species, said diffusional flow restrictor additionally being constructed and arranged to prevent particulate solids in the fluid environment from contacting the metal species.

12. A sensor according to claim 7, further comprising means for removing from the fluid before its contacting with the metal species substantially all metal species-interactive components other than said trace fluid component.

13. A sensor according to claim 12, wherein the metal species-interactive components removing means comprises a chemisorbent medium having sorptive affinity for said metal species-interactive components other than said trace fluid component.

14. A sensor according to claim 7, wherein said means for carrying out functions (i), (ii) and (iii), are constructed and arranged to provide (A) an output gas alarm condition indicative of breakthrough of the trace fluid component, and (B) an output system fault condition indicative of a continuing leak of the trace fluid component when the trace fluid component has consumed a significant portion of the metal species material in the inert porous material.

15. A fluid scrubbing assembly for processing of impurity-containing fluid, comprising:
   a scrubber vessel containing a dry scrubber composition having sorptive affinity for impurity in said impurity-containing fluid;
   means for introducing impurity-containing fluid to the scrubber vessel for contacting with the dry scrubber composition therein to remove impurity from the impurity-containing fluid, and yield treated fluid;
   means for discharging treated fluid from the scrubber vessel;
   a sensor for detection of impurity in the treated fluid, said sensor comprising:
      (I) a piezoelectric crystal having a fundamental resonant frequency in response to an applied oscillating electric field;
      (II) a coating on the piezoelectric crystal of an inert porous material containing a metal species which is reactive with the impurity to yield a solid interaction product of increased mass in relation to mass of the metal species interacting with the impurity to yield said solid interaction product;
      (III) means for applying an oscillating electric field to the piezoelectric crystal which generates an output resonant frequency therefrom; and
      (IV) means for (i) sampling the output resonant frequency of the piezoelectric crystal while said oscillating electric field is applied thereto, (ii) determining the differential frequency rate of change in resonant frequency over time from the fundamental resonant frequency upon formation of said solid interaction product when the metal species interacts with impurity in said treated fluid, and (iii) generating an output indicative of the presence of the impurity in said treated fluid; and
   means for flowing at least a portion of the treated fluid to the sensor for determining, by said output indicative of the presence of impurity, when breakthrough of impurity has occurred in the dry scrubber composition in said vessel;
wherein the coated piezoelectric crystal exhibits a frequency response rate to the impurity in the treated fluid, in the range of from about 0.001 to about 1000 milliHertz/min/(part-per-million of the impurity in the treated fluid).

16. A process for monitoring a fluid stream for determining presence of a selected component therein, said process comprising:
   providing a sensor for detection of the selected component in the fluid stream, said sensor comprising:
      (A) a piezoelectric crystal having a fundamental resonant frequency in response to an applied oscillating electric field; and
      (B) a coating on the piezoelectric crystal of an inert porous material containing a metal species sensor material which is reactive with the selected component to yield a solid interaction product of increased mass in relation to mass of the metal species sensor material interacting with the selected component to yield said solid interaction product;
   applying an oscillating electric field to the piezoelectric crystal which generates an output resonant frequency therefrom;
   sampling the output resonant frequency of the piezoelectric crystal while said oscillating electric field is applied thereto;
   determining the differential frequency rate of change in resonant frequency over time from the fundamental resonant frequency incident to the formation of said solid interaction product when the metal species material interacts with said selected component in said fluid stream; and
   generating an output indicative of the presence of the selected component in said fluid stream;
wherein the coated piezoelectric crystal exhibits a frequency response rate to the selected component in the range of from about 0.001 to about 100,000 milliHertz/min/(part-per-million of the fluid component).

17. A process according to claim 16, wherein the piezoelectric crystal comprises a piezoelectric silica crystal.

18. A process according to claim 16, wherein the coated piezoelectric crystal exhibits a frequency response rate to the selected component in the range of from about 0.01 to about 10,000 milliHertz/min/(part-per-million of the fluid component).

19. A process according to claim 16, wherein the piezoelectric crystal has a fundamental resonant frequency in the range of from 1 Megahertz to 20 Megahertz.

20. A process according to claim 16, wherein the step of generating said output indicative of the presence of the selected component in said fluid stream, comprises determining via a programmed computer a calculated concentration of said selected component in said fluid stream.

21. A process according to claim 20, further comprising controllably flowing at least a portion of the fluid stream at a selected flow rate in contact with the sensor material on said piezoelectric crystal, and determining said calculated concentration of said selected component in said fluid stream.

22. A process according to claim 16, further comprising restricting the flow of the fluid stream to permit only diffusional flow of fluid to the metal species sensor material, and preventing particulate solids in the fluid stream from contacting the metal species sensor material.

23. A process according to claim 16, further comprising removing from the fluid before its contacting with the metal species sensor material substantially all metal species sensor material-interactive components other than said selected component.

24. A process according to claim 23, wherein the metal species sensor material-interactive components are removed by contact of the fluid stream with a chemisorbent medium having sorptive affinity for said sensor material-interactive components other than said selected component.

25. A process according to claim 16, wherein the metal species sensor material comprises a metal oxide or salt.

26. A process according to claim 25, wherein the metal is selected from the group consisting of copper, zinc, calcium, manganese, sodium, silver, iron and chromium.

27. A process according to claim 16, wherein the selected component is a hydride gas.

28. A fluid scrubbing process for treating impurity-containing fluid, comprising:

contacting impurity-containing fluid with a dry scrubber composition to remove impurity from the impurity-containing fluid, and yield treated fluid;

detecting impurity in the treated fluid, by the steps comprising:

providing:

(I) a piezoelectric crystal having a fundamental resonant frequency in response to an applied oscillating electric field; and (II) a coating on the piezoelectric crystal of an inert porous material to provide a coated piezoelectric crystal, the inert porous material containing a metal species which is reactive with the impurity to yield a solid interaction product of changed mass in relation to the initial mass of the metal species interacting with the impurity to yield said solid interaction product, the coated piezoelectric crystal exhibiting a frequency response rate to the impurity in the treated fluid, in the range of from about 0.01 to about 10,000 milliHertz/min/(part-per-million of the impurity in the treated fluid);

applying an oscillating electric field to the piezoelectric crystal which generates an output resonant frequency therefrom;

sampling the output resonant frequency of the piezoelectric crystal while said oscillating electric field is applied thereto;

determining the differential frequency rate of change in resonant frequency over time from the fundamental resonant frequency incident to the formation of said solid interaction product when the metal species interacts with impurity in said treated fluid;

generating an output indicative of the presence of the impurity in said treated fluid; and flowing at least a portion of the treated fluid to the sensor for determining, by said output indicative of the presence of impurity, when breakthrough of impurity has occurred in the dry scrubber composition.

* * * * *

UNITED STATES PATENT AND TRADEMARK OFFICE
CERTIFICATE OF CORRECTION

PATENT NO. : 5,827,947
DATED : October 27, 1998
INVENTOR(S) : Miller et al.

It is certified that error appears in the above-indentified patent and that said Letters Patent is hereby corrected as shown below:

Column 2, line 34 "The results" should be --This results--

Signed and Sealed this

Sixth Day of April, 1999

Attest:

Attesting Officer

Q. TODD DICKINSON

Acting Commissioner of Patents and Trademarks